(12) United States Patent
Rauh

(10) Patent No.: US 7,949,473 B2
(45) Date of Patent: May 24, 2011

(54) METHOD FOR DETECTING ERRONEOUS MEASUREMENT RESULTS OBTAINED WITH ION-SELECTIVE ELECTRODES

(75) Inventor: Jürgen Rauh, Mellingen (CH)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 645 days.

(21) Appl. No.: 11/858,954

(22) Filed: Sep. 21, 2007

(65) Prior Publication Data

US 2008/0077330 A1 Mar. 27, 2008

(30) Foreign Application Priority Data

Sep. 26, 2006 (EP) .................................... 06020084

(51) Int. Cl.
*G01N 33/48* (2006.01)
*G01N 31/00* (2006.01)
*C12Q 1/68* (2006.01)

(52) U.S. Cl. ................. 702/19; 435/6; 436/19

(58) Field of Classification Search .......................... None
See application file for complete search history.

(56) References Cited

U.S. PATENT DOCUMENTS

2003/0062262 A1 4/2003 Mansouri et al.

FOREIGN PATENT DOCUMENTS

EP 0 364 948 A2 4/1990
EP 0 667 522 A2 8/1995

OTHER PUBLICATIONS

Definition of standard deviation. The Penguin Dictionar of Economics, 2003. Retrieved online on Sep. 1, 2010 fromn <<http://www.credoreference.com/entry/penguinecon/standard_deviation>>.*
Kemp, G.J. et al. "Theoretical Aspects of One-Point Calibration: Causes and Effects of Some Potential Errors, and Their Dependence on Concentration", Clinical Chemistry, vol. 30, No. 7, 1984, pp. 1163-1167.

* cited by examiner

*Primary Examiner* — Russell S Negin
(74) *Attorney, Agent, or Firm* — Dinsmore & Shohl LLP

(57) ABSTRACT

A method for measuring the concentration of at least two analytes in a biological liquid sample by using a set of ion selective electrodes is disclosed. The method obtains from the ion selective electrodes first voltage values representative of the concentration of sodium and potassium respectively in those biological samples, and obtains from the ion selective electrodes second voltage values representative of the concentration of sodium and potassium respectively in calibration standards. The method verifies by a predetermined procedure whether each of the second voltage values obtained by measuring the calibration standards has an abnormal value caused by a disturbance of the measurement conditions in one of the ion selective electrodes, and if this is the case, marks with a flag as doubtful the measurement results derived from the first voltage values obtained for the corresponding sample which was measured before measuring the calibration standards for sodium and potassium.

7 Claims, 2 Drawing Sheets

| | | Concentrations measured | | Potential differences measured | | | | Calculations | | Checks | | | Action |
|---|---|---|---|---|---|---|---|---|---|---|---|---|---|
| | | | | Sample measurements | | Calibration measurements | | | | | | | |
| No. | | 11 | 12 | 13 | 14 | 15 | 16 | 17 | 18 | 19 | 20 | 21 | 22 |
| | | Concentration of Sodium [mmol/L] | Concentration of Potassium [mmol/L] | Sample Sodium [mV] | Sample Potassium [mV] | One-point calibration Sodium [mV] | One-point calibration Potassium [mV] | Calculation C1 | Calculation C2 | Check 1 | Check 2 | Check 3 | Action |
| 1 | | | | | | | | | | | | | |
| 2 | | | | | | | | | | | | | |
| A | | 132.6 | 5.52 | 73.021 | 29.376 | 76.205 | 27.228 | 0.000 | 0.091 | NO | Ø | Ø | set no flag |
| B | | 137.9 | 4.63 | 73.966 | 24.963 | 76.191 | 27.137 | 0.014 | 0.091 | NO | Ø | Ø | set no flag |
| C | | 128.0 | 3.93 | 73.539 | 22.324 | 77.576 | 28.548 | 1.385 | 1.410 | YES | YES | YES | set flag |
| D | | 137.9 | 4.32 | 73.992 | 23.255 | 76.204 | 27.163 | 1.372 | 1.385 | YES | YES | NO | set no flag |
| N-1 | | ConcS$_{N-1}$ | ConcP$_{N-1}$ | SS$_{N-1}$ | SP$_{N-1}$ | CS$_{N-1}$ | CP$_{N-1}$ | | | | | | |
| N | | ConcS$_N$ | ConcP$_N$ | SS$_N$ | SP$_N$ | CS$_N$ | CP$_N$ | $\lvert CS_N - CS_{N-1} \rvert$ | $\lvert CP_N - CP_{N-1} \rvert$ | | | | |

*Fig. 1       Table 1*

METHOD FOR DETECTING ERRONEOUS MEASUREMENT RESULTS OBTAINED WITH ION-SELECTIVE ELECTRODES

FIELD OF THE INVENTION

The present invention relates generally to analyzing biological liquid samples, and in particular to a method for measuring the concentration of at least two analytes in a biological liquid sample by means of a set of ion selective electrodes each of which is suitable for measuring one of those analytes, one of those analytes being sodium and another of those analytes being potassium, and wherein the ion-selective electrodes may be part of a clinical chemistry analyzer system.

BACKGROUND OF THE INVENTION

Ion-selective electrode (ISE) techniques are routinely used in the clinical chemistry laboratories for the determination of sodium, potassium, or chloride. These ions are important regulators of various physiological functions, thus their monitoring/determination in patient samples (e.g. serum, plasma, or urine) is of great importance.

The underlying measurement principle is potentiometry. Devices employing ISEs use a measurement electrode, which is ideally selective only for the ion it should measure, and a reference electrode, which delivers a stable potential against which the measurement electrode's potential is read.

The sample (e.g. human serum, plasma, or urine) is placed in the sample channel in front of the ion selective membrane. A potential develops over this membrane, which under ideal circumstances only depends on the activity of the ion to be measured (the analyte).

That potential is derived via the contact pin and read against a stable signal delivered by the reference electrode. This reference electrode is the other half-cell of the measurement circuit.

The potential difference measured between the measurement electrode and the reference electrode is related to the concentration of the ion in question employing the Nernst equation as described e.g. in chapter of the book K Cammann, H Galster "Das Arbeiten mit ionenselektiven Elektroden", 3rd edition, Springer Verlag, 1996.

Each sample measurement consists of two separate measurements: the measurement of the sample material itself, and the subsequent one-point calibration. The one-point calibration is the measurement of a one-point calibrator of known concentration. The results of both, sample and one-point calibration measurement are expressed in millivolt.

These results, together with the electrode slope and other parameters determined during the main calibration (i.e. a two-point calibration), are used for the calculation of the final sample result (i.e. ion concentration), usually expressed in mmol/L (millimole per liter).

In clinical chemistry analyzers from various manufacturers, ISE modules containing sodium, potassium, and chloride selective electrodes are used for the routine determinations of those ions in human body fluid samples (such as serum, plasma, or urine) for diagnostic purposes. These modules allow the simultaneous determination of the analyte concentrations in one measurement from a given sample.

The results generated by such modules are of significant clinical relevance, and therefore care must be taken to ensure result integrity under all circumstances. Thus, the results are subjected to several checks and plausibility controls prior their display on an instrument, or distribution to electronic laboratory information systems.

If, for instance, the signal generated for a given electrode (e.g. sodium) does not fulfill pre-defined criteria for the signal stability over time, a flag is generated and attached to the result informing the physician that the validity of the result may be doubtful. Samples for which flagged measurement results are obtained, are routinely re-analyzed, and for this purpose measurement of the sample in the ISE module is repeated.

Since in clinical chemistry it is very important to obtain accurate measurement results especially of the concentrations of sodium and potassium in biological samples, it is desirable to eliminate even very minute error possibilities.

A possible cause of a measurement error is the alteration of the measurement conditions, e.g. by the appearance of air bubbles in the sample channel.

Another possible cause of a measurement error are electrostatic discharges entering the shielded measuring compartment of an ISE module via waste lines and/or not properly grounded mechanical mounting parts. Such electrostatic discharges can cause shifts in the reference potential.

Such alterations can adversely influence the measurement results, because the potential difference measured between the measurement electrode and the reference electrode e.g. for the one-point calibration is used for the calculation of the concentrations of the analytes (e.g. sodium and potassium) in biological samples.

Deviations of the potential differences measured with ion-selective electrodes caused by relatively large disturbances are detected by known test and plausibility checks implemented in ISE modules. Small deviations of the potential differences measured with ion-selective electrodes as those caused by the above mentioned air-bubbles and electrostatic discharges, however, may remain undetected, and still adversely affect the measurement results.

The detection of small but abnormal deviations of the potential differences measured with ion-selective electrodes is difficult, because some of those deviations are not indicative for any malfunction or problem, but simply correspond to a concentration value which is higher or lower than an expected normal value.

In view of the foregoing, it is desirable to ensure that at one hand all questionable deviations, i.e. deviations of doubtful origin, are identified, and on the other hand, that valid measurement results are not identified as doubtful, since this would lead to unnecessary repetition of (correct) sample measurements, and this causes unnecessary work and expenses and delays in the delivery of the measurement results.

SUMMARY OF THE INVENTION

It is against the above background that the present invention provides a method for measuring the concentration of at least two analytes in a biological liquid sample by means of a set of ion selective electrodes each of which is suitable for measuring one of those analytes, one of those analytes being sodium and another of those analytes being potassium, and the method including steps for detecting deviations of the potential difference measured with the ion-selective electrodes which are caused by disturbances like air-bubbles in the sample channel of the ISE or electrostatic discharges.

In one embodiment a method according to the invention comprises
measuring a series of different biological samples of the same kind with the set of ion selective electrodes;

obtaining from the ion selective electrodes first voltage values in millivolt which are representative of the concentration of sodium and potassium respectively in each of those biological samples;

storing the first voltage values in a suitable form for data processing;

measuring a calibration standard for sodium and potassium with the respective ion selective electrodes after measuring each of the biological samples;

obtaining from the ion selective electrodes second voltage values in millivolt which are representative of the concentration of sodium and potassium respectively in each of those calibration standards;

storing the second voltage values in a suitable form for data processing; and verifying whether each of the second voltage values has an abnormal value caused by a disturbance in the operation of one of the ion selective electrodes, the verifying comprises processing measured second voltages values obtained for successive measurement results corresponding to different samples (N and N−1), and the processing comprises:

(i) calculating and storing the absolute value ($\Delta CS_N = |CS_N - CS_{N-1}|$) of the difference of the second voltage values measured by the electrode for sodium which correspond to a sample (N) and to the immediately preceding sample (N−1), (ii) calculating and storing the absolute value ($\Delta CP_N = |CP_N - CP_{N-1}|$) of the difference of the second voltage values measured by the electrode for potassium which correspond to a sample (N) and to the immediately preceding sample (N−1), (iii) verifying whether each of the calculated and stored absolute values of the changes calculated in steps (i) and (ii) is larger than a first predetermined threshold value, and if the result of this verification is positive, then the processing further comprises:

(iv) verifying whether the calculated and stored absolute values obtained in steps (i) and (ii) differ from each other by an amount which is smaller than a second predetermined threshold value, and if the result of this verification is positive, then the processing further comprises:

(v) verifying whether the calculated absolute values obtained in step (i) for a sample (N) and for the immediately preceding sample (N−1) differ from each other by an amount which is larger than a third predetermined threshold value, and if the result of this verification is positive, then the method further comprises:

marking with a flag as doubtful the measurement results derived from the first voltage values obtained for the corresponding sample which was measured before measuring the calibration standards for sodium and potassium.

In a preferred embodiment of a method according to the invention, the measuring of a calibration standard for sodium and potassium with the respective ion selective electrodes takes place immediately after measuring each of the biological samples, and the marking with a flag as doubtful the measurement results derived from the first voltage values obtained is effected for the corresponding sample which was measured immediately before measuring the calibration standards for sodium and potassium.

In another preferred embodiment of a method according to the invention, the first predetermined threshold value is 0.8 millivolt, the second predetermined threshold value is 0.25 millivolt, and the third predetermined threshold value is 0.25 millivolt.

In another preferred embodiment of a method according to the invention, the first predetermined threshold value is 0.8 millivolt, the second predetermined threshold value is 0.25 millivolt, and the third predetermined threshold value is 0.25 millivolt.

Although not limited thereto, some of the noted advantages obtained with a method according to the invention are as follows.

All questionable deviations of the potential differences measured with the ion-selective electrodes are identified, and flagged. Reporting of questionable results as correct ones is thus reliably prevented.

Valid measurement results are not erroneously identified as doubtful. Erroneous reporting of valid results as doubtful ones and unnecessary repetition of measurements caused by such reports is thus reliably prevented.

The reliability and accuracy of the results of measurement performed with the ion-selective electrodes is ensured in particular when air-bubbles alter the measurement conditions in the measurement chamber and/or electrical disturbances occur, and when other implemented plausibility checks of the operation of the ion-selective electrodes fail.

Any flag already implemented in the analyzer system is suitable for being used as a flag to be attached to a result which is found doubtful by the method according to the invention. It is therefore not necessary to implement a new flag in the software of the analyzer. The risk associated with the implementation of a new flag in the system software and validation efforts with respect to that software are thus avoided.

The method according to the invention does not require any modification of existing system interfaces with laboratory information systems/communication protocols.

These and other features and advantages of the present invention will be apparent from the following detailed description provided hereinafter with reference to the accompanying drawings.

BRIEF DESCRIPTION OF THE DRAWINGS

The subject invention will now be described in terms of its various embodiments with reference to the accompanying drawings. These embodiments are set forth to aid the understanding of the invention, but are not to be construed as limiting.

FIG. 1 shows a table (Table 1) showing in columns 11 to 16 a list of results for measurement results obtained with ion-selective-electrodes for different samples and in columns 17 to 21 results of calculations and checks obtained with a method according to the invention.

Figure 2:
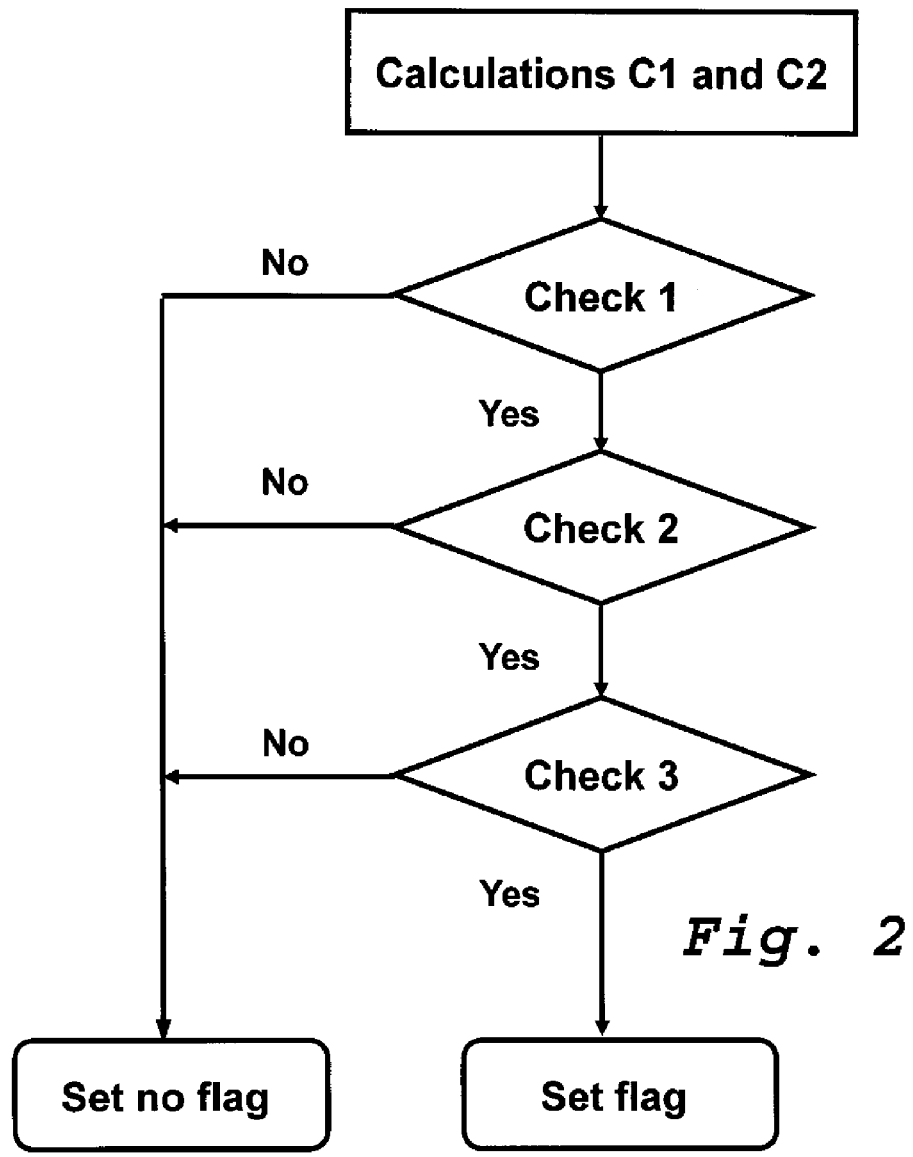
FIG. 2 shows a flow chart illustrating steps of a method according to the invention, and in particular checks 1 to 3 mentioned in Table 1 in FIG. 1.

REFERENCE SYMBOLS USED IN DRAWINGS $SS_N$ potential difference measured with a sodium sensitive ion-selective-electrode for the Nth sample of a series of successively measured samples $ConcS_N$ concentration of sodium calculated on the basis of $SS_N$ $SP_N$ potential difference measured with a potassium sensitive ion-selective-electrode for the Nth sample of a series of successively measured samples $ConcP_N$ concentration of potassium calculated on the basis of $SP_N$ $CS_N$ voltage measured for the sodium one-point calibration for the Nth sample $CS_{N-1}$ voltage measured for the sodium one-point calibration for the (N−1)th sample $CP_N$ voltage measured for the potassium one-point calibration for the Nth sample $CP_{N-1}$ voltage measured for the potassium one-point calibration for the (N−1)th sample C1 calculation of the value $|CS_N - CS_{N-1}|$ C2 calculation of the value $|CP_N - CP_{N-1}|$

DETAILED DESCRIPTION OF THE INVENTION

The method described hereinafter as an example is a method for measuring the concentration of at least two analytes in a biological liquid sample by means of a set of ion selective electrodes each of which is suitable for measuring one of those analytes, one of those analytes being sodium and another of those analytes being potassium. This method includes steps for detecting deviations of potential differences measured which are caused by disturbances of the measurement conditions, e.g. air-bubbles in the sample channel of ion-selective electrodes or electrostatic discharges, and steps for marking with flags measurement results which are found doubtful.

FIG. 1 shows a table (Table 1) showing in columns 11 to 16 a list of results for measurement results obtained with ion-selective-electrodes for different samples and in columns 17 to 21 results of calculations and checks obtained with a method according to the invention. The measurement results indicated in columns 13 to 16 in one of the rows of Table 1 are those obtained for one of a plurality of different samples numbered 1 to N.

The example of a method according to the invention herein described comprises the following steps:

Step (a): Measuring a series of different biological samples of the same kind, e.g. diluted blood samples, with a set of ion selective electrodes, obtaining from the ion selective electrodes voltage values in millivolt which are representative of the concentration of sodium and potassium respectively in each of those biological samples, and storing the latter values in a suitable form for electronic data processing. Columns 13 and 14 of Table 1 show examples of those values for a plurality of measurements of different samples numbered 1 to N. The voltage measured with the sodium measuring electrode for the Nth sample is designated by $SS_N$ and the corresponding value of the concentration of sodium calculated on the basis of $SS_N$ is designated by $ConcS_N$ and is noted in column 11. The voltage measured with the potassium measuring electrode for the Nth sample is designated by $SP_N$ and the corresponding value of the concentration of potassium calculated on the basis of $SP_N$ is designated by $ConcP_N$ and is noted in column 12. The respective values obtained for the N−1 sample are designated in a similar way, but with the subindex N−1.

Step (b): Measuring a calibration standard for sodium and potassium with the respective ion selective electrodes after measuring each of the biological samples according to step (a), obtaining from the ion selective electrodes voltage values in millivolt which are representative of the concentration of sodium and potassium respectively in each of those calibration standards, and storing the latter values in a suitable form for electronic data processing. Columns 15 and 16 of Table 1 show examples of those values associated with corresponding measurements of a plurality of different samples numbered 1 to N. The voltage values indicated in columns 15 and 16 of each row of Table 1 are those associated with or corresponding to the voltage values indicated in columns 13 and 14 of the same row of Table 1. The voltage measured for the sodium one-point calibration for the Nth sample is designated by $CS_N$. The voltage measured for the potassium one-point calibration for the Nth sample is designated by $CP_N$. The respective values obtained for the N−1 sample are designated in a similar way, but with the subindex N−1.

Step (c): Verifying by a predetermined procedure (described in detail hereinafter) whether each of the values in millivolt obtained by measuring the calibration standards according to step (b) has an abnormal value caused by a disturbance in the operation of one of the ion selective electrodes, and if this is the case, then the method further comprises the following step.

Step (d): Marking with a flag as doubtful the measurement results obtained for the corresponding sample which was measured before measuring the calibration standards for sodium and potassium according to step (b).

In one embodiment the measuring of a calibration standard for sodium and potassium with the respective ion selective electrodes according to step (b) takes place immediately after measuring each of the biological samples according to step (a), and the marking with a flag as doubtful the measurement results obtained according to step (d) is effected for the corresponding sample which was measured immediately before measuring the calibration standards for sodium and potassium according to step (b).

The voltage values obtained according to step (a) for a given sample and the voltage values obtained according to step (b) form a set of values of a measurement result for a given sample, e.g. for one of the 1 to N samples mentioned in Table 1.

An example of a predetermined procedure mentioned above in Step (c) for verifying whether the values in millivolt obtained by measuring the calibration standards according to step (b) have an abnormal value comprises processing measured voltages in millivolt obtained according to step (b) for successive measurement results corresponding to different samples (N and N−1), and the processing comprises the following steps:

Step (i): calculating and storing the absolute value ($\Delta CS_N = |CS_N - CS_{N-1}|$) of the difference of the voltages measured by the electrode for sodium which correspond to a sample (N) and to the immediately preceding sample (N−1);

Step (ii): calculating and storing the absolute value ($\Delta CP_N = |CP_N - CP_{N-1}|$) of the difference of the voltages measured by the electrode for potassium which correspond to a sample (N) and to the immediately preceding sample (N−1); and Step (iii): verifying whether each of the calculated and stored absolute values of the changes calculated in steps (i) and (ii) is larger than a first predetermined threshold value, and if the result of this verification is positive, then the processing further includes:

Step (iv): verifying whether the calculated and stored absolute values obtained in steps (i) and (ii) differ from each other by an amount which is smaller than a second predetermined threshold value, and if the result of this verification is positive, then the processing further includes:

Step (v): verifying whether the calculated absolute values obtained in step (i) for a sample (N) and for the immediately preceding sample (N−1) differ from each other by an amount which is larger than a third predetermined threshold value, and if the result of this verification is positive, then the processing further includes:

Step (vi): generating a signal indicating that the measurement results of the sample (N) are doubtful.

In one embodiment, the first predetermined threshold value in Step (iii) is 0.8 millivolt, the second predetermined threshold value in Step (iv) is 0.25 millivolt, and the third predetermined threshold value in Step (v) is 0.25 millivolt.

The threshold values indicated above have been obtained experimentally from experiences with the absolute value of deviations in one-point calibration mV-values. Threshold values which sensibly differ from those indicated above are not adequate for the intended purpose, either because they are insensitive (e.g. using a threshold value of 1.2 mV in Check 1), or too sensitive (e.g. applying a limit of 0.1 in Checks 2 and 3).

Columns 17 and 18 of Table 1 show some of calculation results C1 and C2 obtained with Steps (i) and (ii) for a series of samples 1 to N. For successive samples designated by the letters A, B, C and D numerical values are indicated as examples.

Columns 19 to 21 of Table 1 indicate for samples A, B, C and D the result of the verification according to Step (iii) designated as Check 1, the result of the verification according to Step (iv) designated as Check 2 and the result of the verification according to Step (v) designated as Check 3. The symbol Ø used in Table 1, columns 20 and 21 for samples A and B, means that for these samples the result of Check 2 is not determined. This is so, because according to the flow chart represented by FIG. 2, Check 2 is not carried out, because the result of Check 1 is negative.

FIG. 2 shows a flow chart illustrating steps of the above described method according to the invention, and in particular checks 1 to 3 mentioned in Table 1 in FIG. 1 performed on the basis of the values calculated and stored according to steps (i) and (ii).

As illustrated by FIG. 2 a flag indicative of an abnormal result is only set if the results of Check 1 and Check 2 and Check 3 are positive. If this condition is not satisfied, no flag is set and this is equivalent to recognition of a measurement result as being valid.

As shown by Table 1, all three Checks 1, 2 and 3 provide positive results for the measurement results in the row designated with the letter C, whereas for the measurement results in the rows designated with the letters A, B and D at least one of Checks 1, 2 and 3 provides a negative result.

Comparison of the results in row C, columns 17 and 18, of Table 1 with the results listed in rows B and D, columns 17 and 18 of Table 1 shows that the results for both sodium and potassium in these rows are lower than in row C, although the sample mV values at least for sodium (column 13) are nearly identical. The mV-values for the one-point calibrations of both electrodes are elevated for measurement of row C, columns 17 and 18, compared to those obtained for rows B and D, columns 17 and 18, and approximately by the same amount (1.38 mV, and 1.41 mV, respectively).

The above described method is applicable not only to sodium and potassium, but also to other analytes, e.g. sodium and an analyte other than potassium.

When the laboratory where the ISE measurements are performed on samples starts its daily operation and the measurement values of row 1 of Table 1 are obtained there are no measurement values of an immediately preceding sample. In this case one-point calibration mV-values generated and stored in the system during a main calibration are employed as initial values in order to be able to perform the calculations and verifications of the above described method also for the measurement results in row 1 of Table 1.

Main calibrations are conducted at defined intervals, and it is regarded as good laboratory practices to confirm a calibration by means of quality control samples. Their results are thoroughly scrutinized prior to acceptance, and it is thus ensured that a calibration is correct.

Additionally, several independent checks applied to main calibration results also ensure that the mV-values generated during a main calibration are trustworthy if unflagged and if quality control results are within allowed ranges.

A main calibration procedure is carried out e.g. as follows.

Samples, standard calibration solutions for ISE, or quality control liquids are transferred to the measurement chamber of the ISE-module via the automatic pipetting unit of the clinical diagnostic analyzer the ISE-module belongs to, whereas one-point calibrator liquids are directly sucked from a bottle located close to the ISE-Module and directly supplied to the measurement chamber of the ISE-Module.

Thus, samples or standard calibration solutions for ISE, or quality control liquids are handled differently than the one-point calibrator liquids. This may result in accuracy problems, if not corrected correspondingly. It is e.g. possible that the dilution ratio changes over time on a given system, or that there are variations of dilution ratios actually provided by different systems, especially if a large number of them is considered (e.g. >1000).

To compensate for such differences that may affect the accuracy of the ISE measurement results obtained with the analyzer system, the so called Solution 1-Factor (SOL1F) correction is implemented as described hereinafter.

Predetermined volumes of the following calibration standards are used:

Sol 1 is a calibration standard having a first concentration value;

Cal is another calibration standard having a second concentration value;

Sol 2 is a calibration standard having a third concentration value.

The following Table 2 shows steps and measurements results obtained for the calculation of the above mentioned correction factor SOL1F.

TABLE 2

Steps and measurements results obtained for the calculation of the above mentioned correction factor SOL1F.

| Step | Action preceding measurement with ion-selective electrode | Measurement result obtained with ion-selective electrode |
|---|---|---|
| 1 | First pipetting of Sol 1 | mVSol 1_1 |
| 2 | First sucking of Cal | mVCal_1 |
| 3 | Second pipetting of Sol 1 | mVSol 1_2 |
| 4 | Second sucking of Cal | mVCal_2 |
| 5 | Pipetting of Sol 2 | mVSol_2 |

The measured value mVCal_2 is the start value for one-point calibration checks according to the invention when no preceding measurement values are available, e.g. at the beginning of the daily operation of the ISE module.

Using the one-point calibration measurement result mVCal_2 obtained in step 4 of the above sequence of steps 1 to 5 ensures that only such results are used as starting point for the subsequent checks which have been checked for their integrity by different means.

After the measurements of the above mentioned steps 1-5 are completed, the following calculations are performed:
Calculation of Slope according to:

$$\text{Slope} = \frac{mVSol1\_2 - mVSol\_2}{\log \frac{C_{Sol1}}{C_{Sol2}}} \quad (1)$$

with
$C_{Sol1}$=concentration of the ion in Sol 1 (e.g. Sodium=150 mM),
$C_{Sol2}$=concentration of the ion in Sol 2 (e.g. Sodium=110 mM), and
log=logarithms to base 10.

The dimension of the Slope is mV/decade.

The resulting slope is checked whether it is within the allowed limits, which themselves are specified in the corresponding test settings of the system.

The SOL1-Factor is calculated according to:

$$SOL1F = \frac{mVSol1\_1 + mVSol1\_2}{mVCal\_1 + mVCal\_2} \quad (2)$$

The correction factor SOL1F has no dimension.

Sol1F is a correction factor for calculation of concentration values.

$$ConcMeas = C_{Sol1} * 10^{\frac{mVSol1\_2 - mVCal2 * SOL1F}{Slope}} \quad (3)$$

The same variables as in (1) and (2) above are used.

ConcMeas is the calculated value of the concentration of Sol 1.

The calculated value ConcMeas is obtained using the values for the Slope and SOL1F as they have been calculated by equations (1) and (2).

Since Sol 1 is employed for the measurement the target concentration is known.

Using Sodium as an example, this is 150 mmol/L. Conc.Meas is now checked for its deviation from that value according to 148.8 mmol/L<Conc.Meas<151.2 mmol/L  (4)

If this check is fulfilled the main calibration provides a sound basis for future one-point calibrations and ensures the reliability and accuracy of the measurement results obtained. Otherwise, i.e. if the above check (4) is not fulfilled, a flag is attached to all results generated with this main calibration.

Although various embodiments of the invention have been described using specific terms, such description is for illustrative purposes only, and it is to be understood that changes and variations may be made without departing from the spirit or scope of the following claims.

The invention claimed is:

1. A method for measuring the concentration of at least two analytes in a biological liquid sample by means of a set of ion selective electrodes each of which is suitable for measuring one of those analytes, one of those analytes being sodium and another of those analytes being potassium, said method comprising:
measuring a series of patient biological liquid samples, each of the samples being of the same kind, with said set of ion selective electrodes to obtain
from the ion selective electrodes first voltage values in millivolt which are representative of the concentration of sodium and potassium respectively in each of the patient biological liquid samples;
storing the first voltage values in a suitable form for data processing;
measuring a calibration standard for sodium and a calibration standard for potassium each with a respective one of the ion selective electrodes after measuring each of said patient biological liquid samples to obtain
from the ion selective electrodes second voltage values in millivolt which are representative of the concentration of sodium in the calibration standard for sodium and potassium in the calibration standard for potassium respectively, wherein each of the second voltage values obtained corresponds to a respective one of the patient biological liquid samples;
storing the second voltage values in a suitable form for data processing; and
verifying whether each of said second voltage values has an abnormal value caused by a disturbance in the operation of one of the ion selective electrodes, said verifying comprises processing each of said second voltages values obtained for successive measurement results corresponding to different ones of the patient biological liquid samples, and said processing comprises:
(i) calculating and storing the absolute value $(\Delta CS_N = |CS_N - CS_{N-1}|)$ of the difference of the second voltage values measured by the electrode for sodium which correspond to a biological liquid sample (N) and to the immediately preceding biological liquid sample (N−1) in the series of patient biological liquid samples,
(ii) calculating and storing the absolute value $(\Delta CP_N = |CP_N - CP_{N-1}|)$ of the difference of the second voltage values measured by the electrode for potassium which correspond to the biological liquid sample (N) and to the immediately preceding biological liquid sample (N−1) in the series of patient biological liquid samples,
(iii) verifying whether each of the calculated and stored absolute values of the changes calculated in steps (i) and (ii) is larger than a first predetermined threshold value, and if the result of this verification is positive, then said processing further comprises:
(iv) verifying whether the calculated and stored absolute values obtained in steps (i) and (ii) differ from each other by an amount which is smaller than a second predetermined threshold value, and if the result of this verification is positive, then said processing further comprises:
(v) verifying whether the calculated absolute values obtained in step (i) for the biological liquid sample (N) and for the immediately preceding biological liquid sample (N−1) in the series of patient biological liquid samples differ from each other by an amount which is larger than a third predetermined threshold value, and if the result of this verification is positive, and
(vi) generating a signal indicating that measurement results of the biological liquid sample (N) are doubtful, and then said method further comprises:
marking as doubtful the measurement results derived from the first voltage values which correspond to the biological liquid sample (N) of the series of patient biological liquid samples with a flag when the signal is generated.

2. A method according to claim 1, wherein said measuring of the calibration standard for sodium and the calibration standard for potassium each with the respective one of the ion selective electrodes takes place immediately after measuring each respective one of said patient biological liquid samples, and said marking with a flag as doubtful the measurement results derived from the first voltage values obtained is effected for the corresponding sample which was measured immediately before measuring the calibration standard for sodium and the calibration standard for potassium.

3. A method according to claim 1, wherein said first predetermined threshold value is 0.8 millivolt, said second predetermined threshold value is 0.25 millivolt, and said third predetermined threshold value is 0.25 millivolt.

4. A method according to claim 2, wherein said first predetermined threshold value is 0.8 millivolt, said second predetermined threshold value is 0.25 millivolt, and said third predetermined threshold value is 0.25 millivolt.

5. A method according to claim 1, wherein if there are no second voltage values for the immediately preceding biological liquid sample (N−1), said method further comprises employing voltage values generated during a main calibration as the second voltage values for the immediately preceding biological liquid sample (N−1).

6. A method according to claim 5, wherein each respective one of the voltage values is generated during the main calibration as follows:
 obtaining a first voltage value (mVSol1_1) of a first calibration standard having a first known concentration value ($C_{sol1}$) with the respective one of the ion-selective electrodes;
 obtaining a first voltage value (mVCal_1) of a second calibration standard with the respective one of the ion-selective electrodes;
 obtaining a second voltage value (mVSol1_2) of the first calibration standard having the first known concentration with the respective one of the ion-selective electrodes;
 obtaining a second voltage value (mVCal_2) of the second calibration standard with the respective one of the ion-selective electrodes;
 obtaining a voltage value (mVSol_2) of a third calibration standard having a second known concentration value ($C_{sol2}$) with the respective one of the ion-selective electrodes, said second known concentration being different from the first known concentration;
 calculating a slope with logarithms (log) to base 10 according to:

$$\text{Slope} = \frac{mVSol1\_2 - mVSol\_2}{\log \frac{C_{Sol1}}{C_{Sol2}}};$$

calculating a dimensionless correction factor (SOL1F) according to:

$$SOL1F = \frac{mVSol1\_1 + mVSol1\_2}{mVCal\_1 + mVCal\_2};$$

calculating a correction factor (ConcMeas) according to:

$$ConcMeas = C_{Sol1} * 10^{\frac{mVSol1\_2 - mVCal2*SOL1F}{Slope}}; \text{ and}$$

using the voltage value (mVSol_2) of the third calibration standard checking as the respective one of the voltage values generated during the main calibration if the correction factor (ConcMeas) does not deviate from the first known concentration value ($C_{sol1}$) by more than a standard deviation.

7. A method according to claim 6, further comprises attaching a flag to all results generated that used the voltage value (mVSol_2) of the third calibration standard if the correction factor (ConcMeas) deviates from the first known concentration value (CSol1) by more than a standard deviation.

\* \* \* \* \*

UNITED STATES PATENT AND TRADEMARK OFFICE
CERTIFICATE OF CORRECTION

PATENT NO. : 7,949,473 B2  
APPLICATION NO. : 11/858954  
DATED : May 24, 2011  
INVENTOR(S) : Jurgen Rauh Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 702 days.

Signed and Sealed this
Twenty-sixth Day of July, 2011

David J. Kappos
*Director of the United States Patent and Trademark Office*